US011468992B2

(12) United States Patent
Pulicharam et al.

(10) Patent No.: US 11,468,992 B2
(45) Date of Patent: Oct. 11, 2022

(54) PREDICTING ADVERSE HEALTH EVENTS USING A MEASURE OF ADHERENCE TO A TESTING ROUTINE

(71) Applicant: Harmonize Inc., San Mateo, CA (US)

(72) Inventors: Juvairiya Saidu Pulicharam, Rolling Hills Estates, CA (US); Kevin Zhao, Pacifica, CA (US); Keeyong Han, San Jose, CA (US); Artem Petrov, Pleasanton, CA (US); Yifan Jiang, Redwood City, CA (US)

(73) Assignee: HARMONIZE INC., San Francisco, CA (US)

( * ) Notice: Subject to any disclaimer, the term of this patent is extended or adjusted under 35 U.S.C. 154(b) by 0 days.

(21) Appl. No.: 17/167,989

(22) Filed: Feb. 4, 2021

(65) Prior Publication Data
US 2022/0246296 A1 Aug. 4, 2022

(51) Int. Cl.
*G16H 50/20* (2018.01)
*G16H 50/30* (2018.01)
*G06N 20/00* (2019.01)
*G06N 5/04* (2006.01)

(52) U.S. Cl.
CPC .............. *G16H 50/20* (2018.01); *G06N 5/04* (2013.01); *G06N 20/00* (2019.01); *G16H 50/30* (2018.01)

(58) Field of Classification Search
None
See application file for complete search history.

(56) References Cited

U.S. PATENT DOCUMENTS

| | | |
|---|---|---|
| 5,920,263 A | 7/1999 | Huttenhoff et al. |
| 8,165,893 B1 | 4/2012 | Goldberg et al. |
| 8,484,085 B2 | 7/2013 | Wennberg |
| 9,368,014 B1 | 6/2016 | Bittman |
| 9,375,142 B2 | 6/2016 | Schultz et al. |
| 10,531,838 B2 | 1/2020 | Barretto et al. |
| 10,748,656 B1 | 8/2020 | Zhao et al. |
| 2008/0077435 A1 | 3/2008 | Muradia |
| 2008/0288023 A1 | 11/2008 | John |
| 2010/0218132 A1 | 8/2010 | Soni et al. |
| 2011/0021140 A1 | 1/2011 | Binier |
| 2012/0116180 A1 | 5/2012 | Rothman et al. |
| 2012/0221634 A1 | 8/2012 | Treu et al. |
| 2012/0245464 A1 | 9/2012 | Tran |
| 2012/0259652 A1 | 10/2012 | Mallon et al. |
| 2012/0266251 A1 | 10/2012 | Birtwhistle et al. |
| 2013/0093829 A1 | 4/2013 | Rosenblatt et al. |
| 2013/0162160 A1 | 6/2013 | Ganton et al. |
| 2014/0067426 A1 | 3/2014 | Neff |
| 2014/0118159 A1 | 5/2014 | Fish et al. |
| 2014/0121487 A1 | 5/2014 | Faybishenko et al. |
| 2014/0275824 A1 | 9/2014 | Couse |
| 2014/0378863 A1 | 12/2014 | Schafer |
| 2015/0056589 A1 | 2/2015 | Zhang et al. |
| 2015/0112452 A1 | 4/2015 | He et al. |
| 2015/0289809 A1 | 10/2015 | Pacione et al. |
| 2015/0370994 A1 | 12/2015 | Madan et al. |
| 2016/0022162 A1 | 1/2016 | Ong et al. |
| 2017/0012929 A1 | 1/2017 | Shah |
| 2017/0140120 A1 | 5/2017 | Thrower |
| 2017/0351504 A1 | 12/2017 | Riedl |
| 2018/0035927 A1 | 2/2018 | Cronin et al. |
| 2018/0122509 A1 | 5/2018 | Christiansson |
| 2018/0181720 A1 | 6/2018 | Ensey et al. |
| 2018/0192965 A1 | 7/2018 | Rose et al. |
| 2018/0336530 A1 | 11/2018 | Johnson et al. |
| 2019/0109822 A1 | 4/2019 | Clark et al. |
| 2019/0216350 A1 | 7/2019 | Sullivan et al. |
| 2020/0051674 A1 | 2/2020 | Long et al. |

FOREIGN PATENT DOCUMENTS

WO WO-2020185938 A1 9/2020

OTHER PUBLICATIONS

Mulvaney, Shelagh A., et al. "Using mobile phones to measure adolescent diabetes adherence." Health Psychology 31.1 (2012): 43.*
Co-pending U.S. Appl. No. 16/932,634, inventors Zhao; Kevin et al., filed Jul. 17, 2020.
Fornichev et al. "Survey and Systematization of Secure Device Pairing," IEEE Communications Surveys & Tutorials, vol. 20, No. 1, First Quarter 2018, pp. 517-550 (2018).
PCT/US2020/022158 International Search Report and Written Opinion dated Jun. 12, 2020.
U.S. Appl. No. 16/442,277 Notice of Allowance dated Jun. 4, 2020.
U.S. Appl. No. 16/442,277 Office Action dated Jan. 28, 2020.
U.S. Appl. No. 16/442,277 Office Action dated Sep. 16, 2019.
Sundararajan et al. New ICD-10 version of the Charlson Comorbidity Index predicted in-hospital mortality. Journal of Clinical Epidemiology 57:1288-1294 (2004).
CareConnect/MyChart Patient Entered Data Flowsheets—Blood Pressure, Texas Health Resources (2017). 6 pages.
Co-pending U.S. Appl. No. 17/472,494, inventors Zhao; Kevin et al., filed Sep. 10, 2021.
Lee et al. A Theory of Classifier Combination: The Neural Network Approach. Proceedings of 3rd International Conference on Document Analysis and Recognition, 1995, pp. 42-45 vol. 1. Added to IEEE Xplore Aug. 6, 2002.
U.S. Appl. No. 16/932,634 Office Action dated Jan. 21, 2022.
PCT/US2022/015317 International Search Report and Written Opinion dated May 4, 2022.

\* cited by examiner

*Primary Examiner* — G Steven Vanni
(74) *Attorney, Agent, or Firm* — Wilson Sonsini Goodrich & Rosati

(57) ABSTRACT

The present disclosure describes systems and methods for predicting adverse health events of patients. In one embodiment, a system obtains a dataset including a plurality of values for each of a plurality of health measurements. The system can obtain the dataset in real-time or substantially real-time after a patient has taken the plurality of health measurements. The system can also obtain metadata about the dataset. The metadata may include a measure of the patient's adherence or non-adherence to a testing routine. The measure of non-adherence may indicate, for example, the quantity of days in a particular time period that the patient failed to conduct the testing routine. The system can apply an algorithm to the dataset and the metadata to generate a risk score. The risk score may indicate the likelihood that the subject will experience an adverse health event.

20 Claims, 15 Drawing Sheets

Baseline Risk Scoring (1)

TOTAL: ~81

Chronic Conditions (39)

| Condition | Score |
|---|---|
| MI | +1 |
| CHF - Level I | +1 |
| CHF - Level II (Symptomatic) | +2 |
| CHF - Level III (EF < 35%) | +3 |
| Afib | +1 |
| PAD | +1 |
| CVA or TIA | +1 |
| Dementia - Level I (SLUMS score < 27) | +1 |
| Dementia - Level II SLUMS score < 21) | +2 |
| COPD | +1 |
| Cigarette Smoker | +1 |
| Hypertension | +1 |
| CAD | +1 |
| Connective Tissue disease | +1 |
| Peptic Ulcer disease | +1 |
| Liver disease - Level I | +1 |
| Liver disease - Level II | +3 |
| DM Level I (established; asymptomatic) | +1 |
| DM Level II (A1c > 9% OR complications) | +2 |
| Hemiplegia | +2 |
| CKD - Level I (Stage III or greater) | +1 |
| CKD - Level II (on dialysis) | +2 |
| AIDS | +6 |

| Condition | Score |
|---|---|
| Chronic Pain | +1 |
| Mental illness other than | +2 |
| Depression PHQ-9: >10 points | +2 |
| Morbid Obesity (BMI >= 40 kg/m2 or having a BMI >=35 kg/m2 AND experiencing obesity-related health conditions) | +1 |
| Polypharmacy - Level I (greater than 4 medications) | +1 |
| Polypharmacy - Level II (greater than 7 medications) | +2 |
| No annual wellness visit | +1 |

Medical System Utilization (7)

| Item | Score |
|---|---|
| 3 or more ED visits | +2 |
| Readmission | +2 |
| 1 hospitalization chronic cond | +2 |
| Multiple Providers/Specialists | +1 |

Oncology (12)

| Item | Score |
|---|---|
| Solid tumor localized | +2 |
| Solid tumor Metastatic | +6 |
| Leukemia | +2 |
| Lymphoma | +2 |

Falls (3)

| Item | Score |
|---|---|
| Had a fall in the last 12 months | +2 |
| Fall Risk MAHC - 10 Score: > 4 | +1 |
| Diagnosis (3 or more co-existing) | +1 |
| Prior history of falls within 3 months | +1 |
| Incontinence | +1 |
| Visual impairment | +1 |
| Impaired functional mobility | +1 |
| Environmental hazards | +1 |
| 4 or more medications including OTC | +1 |
| Pain affecting level of function | +1 |
| Cognitive impairment | +1 |

FIG. 5A

Baseline Risk Scoring (2)

TOTAL: ~81

Social Determinants (9)

| | |
|---|---|
| Neighborhood is below 150% of poverty level | +2 |
| Neighborhood is below 50% of poverty level | +1 |
| Food insecurity (In the last year the patient went hungry because they could not afford food, or did not have food available) | +2 |
| Insufficient Access to Care (Missed a medical appointment -Doctor's appointment, Dialysis treatment, or Urgent Care, etc.- because of a lack of transportation to these appointments.) | +1 |
| Lives Alone | +1 |
| Language barriers (ESL, difficulty reading, etc.) | +1 |
| Not following up with PCP | +1 |
| Not following up with Specialists | +1 |

Patient Subjective Health (3)

| | |
|---|---|
| *Identification of Seniors At Risk (ISAR) score >2* | +3 |
| 1. Have you needed help on a regular basis (from: home care, home nurse, relatives or others) | +1 |
| 2. Have you needed more help (i.e. for personal care) than usual to be able to take care of yourself? | +1 |
| 3. Have you been hospitalized for one or more days during the last 6 months? | +1 |
| 4. Do you have trouble with your vision? | +1 |
| 5. Do you usually have serious memory problems? | +1 |
| 6. Do you use 4 or more medications? | +1 |
| *If 3+ of these questions are yes, then we add 3 to the baseline score* | |

Labs (4)

| | |
|---|---|
| Anemia (Hgb <10 g/dL) | +1 |
| Albumin (< 3 g/dL) | +1 |
| LDL-C (>70 mg/dL) | +1 |
| Vitamin D (<12 ng/mL) | +1 |

Age (4)

| | |
|---|---|
| 50 – 59 | +1 |
| 60 – 69 | +2 |
| 70 – 79 | +3 |
| 80+ | +4 |

Other (Illnesses to check)

FIG. 5B

Monthly Risk Score

| Category | MAX | Example |
|---|---|---|
| Vital Score: | | |
| Proportion of Blood Pressure (dia) OOR | 1 | 0.1 |
| Proportion of Blood Pressure (sys) OOR | 1 | 0.0 |
| Proportion of SpO2 OOR | 1 | 0.0 |
| Proportion of HR OOR | 1 | 0.0 |
| Proportion of Weight OOR | 1 | 0.5 |
| Proportion of Glucose OOR | 1 | 0.0 |
| Escalations/Submissions | 1 | 0.3 |
| Interventions/Submissions | 1 | 0.2 |
| Non Adherence Score | | |
| No submission days/days in month | 1 | 0.1 |
| TOTAL | 9 | 1.2 |
| MONTHLY RISK SCORE = TOTAL x 10 | 90 | 12 |

OOR % is the proportion of vitals Out Of Range
Minimum Score = 0 when the patient submitted all days of the month, and did not alert.
If the patient did not submit during the month, total score = 10 (Non-Adherence: 10, Vital: 0)
In theory, max score 90.

Patient-specific weights are assigned to all data points collected

Example: Patient Jane Doe, in June 20 had 10 % BP(dia) OOR, 50% Weight OOR, 30% Escalation/Submission, 20% Interventions/Submissions and 10% No submissions days

MM Score = (0.1 + 0.5 + 0.3 + 0.2 + 0.1)*10
MM Score = 12

FIG. 6

Health Information

| Chronic Conditions | | Medical System Utilization | |
|---|---|---|---|
| MI | Yes | 3 or more ED visits | Yes |
| CHF | Level III | Readmission | Yes |
| PAD | No | 1 hospitalization chronic cond | No |
| CVA or TIA | NO DATA | Multiple Providers/Specialists | NO DATA |
| Dementia | Level II | | |
| COPD | No | Oncology | |
| Cigarette Smoker | Yes | Solid tumor localized | No |
| Hypertension | Yes | Solid tumor Metastatic | No |
| CAD | NO DATA | Leukemia | No |
| Connective Tissue disease | No | Lymphoma | NO DATA |
| Peptic Ulcer disease | No | | |
| Liver disease | Level I | Falls | |
| DM | Level II | Had a fall in the last 12 months | Yes |
| Hemiplegia | NO DATA | Fall Risk | Yes |
| CKD | Level I | Diagnosis | No |
| AIDS | No | Prior history of falls within 3 months | No |
| Memory Problem | Yes | Incontinence | Level II |
| Chronic Pain | Yes | Visual impairment | No |
| Mental Illness other than Depression | No | Impaired functional mobility | Yes |

FIG. 10A

| | | | |
|---|---|---|---|
| Depression PHQ-9 | Yes | Environmental hazards | Yes |
| Morbid Obesity | Yes | Pain affecting level of function | NO DATA ⚠ |
| Polypharmacy | No | Cognitive impairment | No |
| Annual wellness not done | No | | |

Other Risk Factors

Social Determinants

| | | | |
|---|---|---|---|
| Medication non-adherence | No | Certain zip codes | Yes |
| | | Food insecurity | No |
| | | Insufficient Access to Care | No |

Labs

| | | | |
|---|---|---|---|
| Anemia | No | Lives Alone | NO DATA ⚠ |
| Albumin | No | Language barriers | Yes |
| LDL-C | Yes | Not following up with PCP | No |
| Vitamin D | NO DATA ⚠ | Not following up with Specialists | Yes |

Patient Subjective Health

| | |
|---|---|
| Identification of Seniors At Risk | No |
| 1. Have you needed help on a regular basis (from: home care, home nurse, relatives or others)? | Yes |
| 2. Have you needed more help (i.e. for personal care) than usual to be able to take care of yourself? | No |
| 3. Have you been hospitalized for one or more days during the last 6 months? | NO DATA ⚠ |
| 4. Do you have trouble with your vision? | Yes |
| 5. Do you usually have serious memory problems? | No |

FIG. 10A cont'd

Vaccinations

| Vaccine | Status | Added By | Vaccination Date |
|---|---|---|---|
| Flucelvax Quadrivalent 0.5 ML Intramuscular Suspension Prefilled Syringe (Influenza) | Completed | | 09/29/20 |
| Flucelvax Quadrivalent Intramuscular Suspension (Influenza) | Completed | | 10/01/19 |
| Fluad 0.5 ML Intramuscular Suspension Prefilled Syringe (No longer available) (Influenza) | Completed | | 09/19/18 |
| Fluad 0.5 ML Intramuscular Suspension Prefilled Syringe (No longer available) (Influenza) | Completed | | 09/18/18 |
| Flucelvax SUSP (No longer available) (Influenza) | Completed | | 10/02/17 |
| Flucelvax Quadrivalent Intramuscular Suspension (Influenza) | Completed | | 10/02/17 |
| Influenza (No longer available) | Completed | | 10/16/15 |
| Influenza (No longer available) | Completed | | 10/17/14 |
| Pneumococcal polysaccharide vaccine, 23 valent (PPSV) | Completed | | 10/17/14 |
| Pneumovax 23 25 MCG/0.5ML Injection Injectable (PPSV) | Completed | | 10/17/14 |

FIG. 10B

Atorvastatin Calcium 80 MG Oral Tablet
100 Tablet, TAKE 1 TABLET AT BEDTIME, 2 refills, Evaluate: 25-Oct-2021

Cilostazol 100 MG Oral Tablet
200 Tablet, TAKE 1 TABLET BY MOUTH TWICE DAILY, 2 refills, Evaluate: 19-Aug-2021 glipiZIDE 10 MG Oral Tablet
60 Tablet, TAKE 1 TABLET BY MOUTH TWICE DAILY, 3 refills, Evaluate: 02-Jul-2021

TRUEplus Pen Needles 32G X 4 MM MISC (No longer available)
200 Each, Miscellaneous, USE TO INJECT INSULIN ONCE DAILY, 3 refills, Evaluate: 11-Jun-2021

Accu-Chek Guide In Vitro Strip
1 100 Strip Box, Strip, USE TWICE DAILY, 1 refill, Evaluate: 11-Jun-2021

Accu-Chek FastClix Lancets
2 102 Unit Box 102, TESTING 2-3 TIMES DAILY, 1 refill, Evaluate: 11-Jun-2021

Famotidine 40 MG Oral Tablet
100 Tablet, TAKE ONE TABLET BY MOUTH ONCE DAILY AS DIRECTED, 1 refill, Evaluate: 11-Jun-2021

Calcitriol 0.25 MCG Oral Capsule
90 Capsule, TAKE 1 CAPSULE ONCE DAILY, 1 refill, Evaluate: 23-May-2021

Esomeprazole Magnesium 40 MG Oral Capsule Delayed Release
90 Capsule, Capsule Delayed Release, TAKE ONE CAPSULE BY MOUTH ONCE DAILY, 1 refill, Evaluate: 02-May-2021

Gabapentin 600 MG Oral Tablet
200 Tablet, TAKE 1 TABLET TWICE DAILY, NO REFILLS, Evaluate: 03-Feb-2021 oxyCODONE-Acetaminophen 10-325 MG Oral Tablet
90 Tablet, TAKE 1 TABLET EVERY 8 HOURS AS NEEDED FOR PAIN, NO REFILLS, Evaluate: 29-Jan-2021

Lantus SoloStar 100 UNIT/ML Subcutaneous Solution Pen-Injector
5 5 x 3 ML Pen, Solution Pen-Injector, inject 50 units at bedtime and increase by 2 units every 5 day if 5 day morning average is greater than 130 mg/dL. Max daily dose 70 units, 1 refill, Evaluate

...CLINICAL QUALITY ALERT...
Sa h. The patient was non-adherent to these meds and failed 3-vdoc measures in 2019. Please address ASAP story=said(Reported), Evaluate

Basaglar KwikPen 100 UNIT/ML Subcutaneous Solution Pen-Injector
14 3 ML Pen, Solution Pen-Injector, Inject 50 Units at bedtime, NO REFILLS, Evaluate: 01-Feb-2020

FIG. 10C

PREDICTING ADVERSE HEALTH EVENTS USING A MEASURE OF ADHERENCE TO A TESTING ROUTINE

BACKGROUND

Hospitalizations and other adverse health events may be costly and may harm a person's health. It may be beneficial to avoid hospitalizations and other adverse health events by intervening before they occur.

SUMMARY

The present disclosure describes systems and methods for predicting adverse health events of patients. In some embodiments, a system obtains a dataset including a plurality of values for each of a plurality of health measurements taken by a patient. The plurality of health measurements may be a part of a testing routine that the patient conducts on a daily basis. The system can obtain the dataset in real-time or substantially real-time after the patient has taken the plurality of health measurements. The system can also obtain metadata about the dataset. The metadata may include a measure of the patient's adherence or non-adherence to the testing routine. The measure of non-adherence may indicate, for example, the quantity of days in a particular time period that the patient failed to conduct the testing routine. The system can apply an algorithm to the dataset and the metadata to generate a risk score. The risk score may indicate the likelihood that the subject will experience an adverse health event (e.g., a health event that leads to a hospitalization).

The system described herein provides at least two improvements to the technical field of diagnostic and preventive medicine. First, the use of real-time or substantially real-time health data may result in more accurate and timely predictions of adverse health events than the use of outdated data because real-time data reflects patients' current health. Previous systems for predicting adverse health events may have instead relied on hospital data or claims data that did not reflect changes to patients' health after leaving the hospital. Second, the use of health data obtained over a long period of time (e.g., weeks to months) may allow the system described herein to track trends in a patient's health over time. The system described herein is also unconventional in that it considers a patient's adherence to a testing routine in predicting adverse health events of the patient.

In one aspect, the present disclosure provides a method for predicting an adverse health event of a subject, comprising: (a) obtaining (1) a dataset comprising a plurality of values for each of a plurality of health measurements taken by the subject and (2) metadata about the dataset, wherein the metadata comprises a measure of adherence to a testing routine comprising the plurality of health measurements; (b) generating a plurality of intermediate scores based on the dataset and the metadata; (c) applying a plurality of weights to the plurality of intermediate scores to generate a risk score, wherein the risk score is indicative of whether the subject will experience the adverse health event; and (d) outputting the risk score on a graphical user interface of a computing device.

In some embodiments, (a) is performed in real-time or substantially real-time after the subject has taken the plurality of health measurements.

In some embodiments, the dataset and the metadata are obtained from a remote computing device of the subject.

In some embodiments, each weight of the plurality of weights is associated with one of the plurality of health measurements. In some embodiment, the plurality of weights is specific to the subject. In some embodiments, the plurality of weights is based at least in part on a medical history of the subject.

In some embodiments, (c) comprises processing the plurality of intermediate scores with a machine learning algorithm. In some embodiments, the machine learning algorithm comprises a classifier. In some embodiments, the machine learning algorithm is a regression algorithm.

In some embodiments, (b) further comprises determining, for each of the plurality of health measurements, a proportion of the plurality of values that falls outside a range associated with the health measurements. In some embodiments, the measure of adherence is based at least in part on a quantity of missing values in the plurality of values. In some embodiments, the range is a patient-specific range. In some embodiments, the range is based at least in part on a medical history of the subject. In some embodiments, the range is based at least in part on a baseline value for the subject.

In some embodiments, the plurality of health measurements comprises diastolic blood pressure, systolic blood pressure, oxygen saturation, heart rate, weight, or glucose.

In some embodiments, the method further comprises determining a qualitative risk level for the risk score based on a distribution of risk scores of a plurality of subjects including the subject.

In some embodiments, each of the plurality of weights is the same.

In some embodiments, at least two of the plurality of weights are different.

In some embodiments, the subject took the plurality of health measurements no more than 30 days before (a).

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5A and FIG. 5B show factors that contribute to the baseline risk score, according to some embodiments;

FIG. 6 shows the calculation of a risk score, according to some embodiments;

FIGS. 10A, 10B, and 10C show a patient profile.

DETAILED DESCRIPTION

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The terms "patient" and "subject," as used herein, generally refer to a person who is undergoing medical testing or treatment. The medical testing or treatment may occur in a medical facility or in the patient's home. The medical testing or treatment may or may not be related to a particular condition or disease. The terms patient and subject are used interchangeably in this disclosure.

Figure 1:
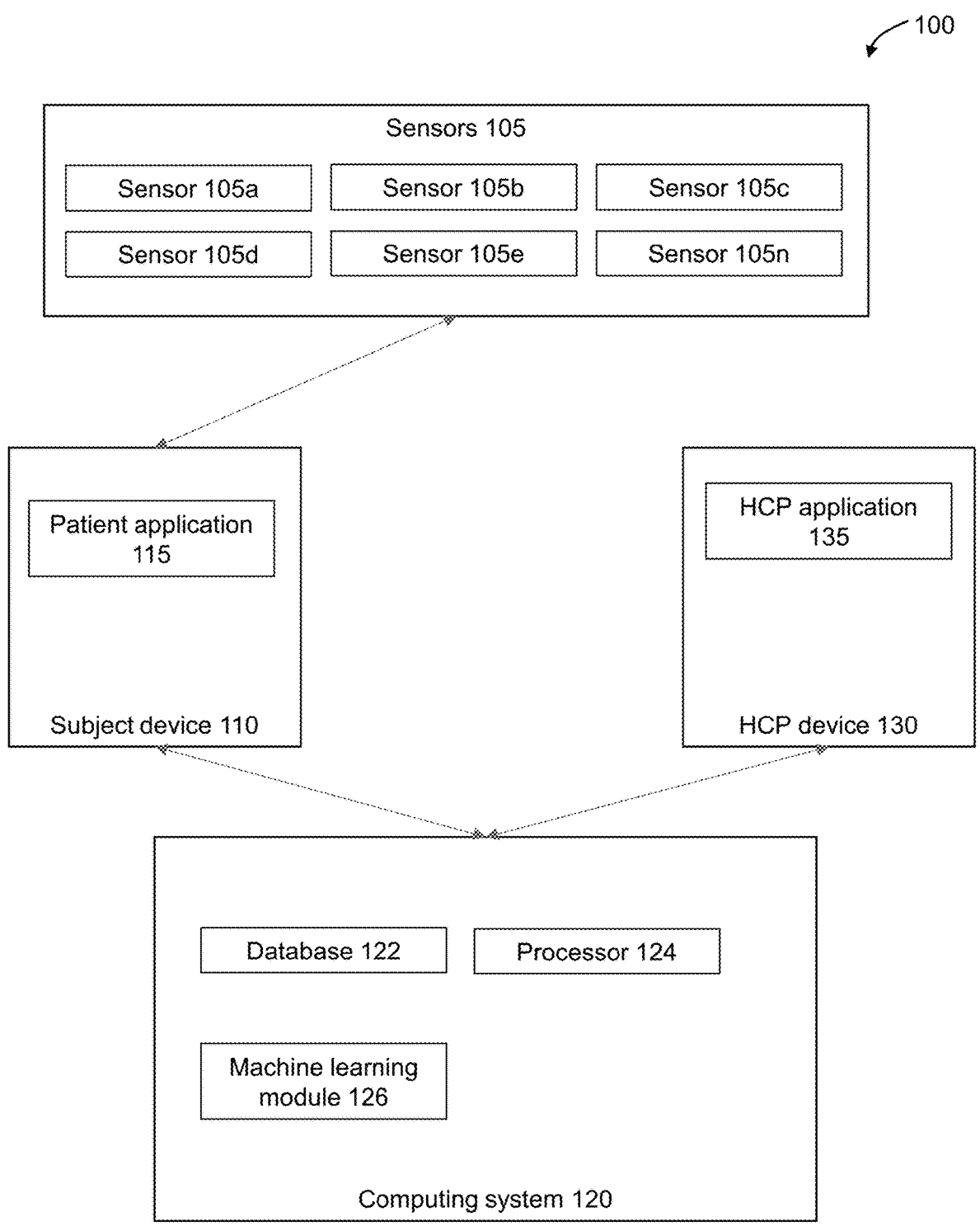
FIG. 1 schematically illustrates a health management platform, according to some embodiments.

FIG. 1 schematically illustrates a health management platform 100, according to some embodiments. The platform 100 may have a patient-facing layer including health sensors 105, a patient device 110, and a patient application 115. The patient-facing layer can facilitate the acquisition of health measurement data by the patient. The platform 100 may also have an analytics layer including a computing system 120, a database 122, a processor 124, and a machine learning module 126. The analytics layer can process the health measurement data to generate predictions, analytics, alerts, and visualizations. The platform 100 may also have a health care provider (HCP)-facing layer including an HCP device 130 and an HCP application 135. The HCP-facing layer may permit an HCP to consume the analytics, alerts, and visualizations generated by the analytics layer.

Patient-Facing Layer

The health sensors 105 may be one or more of the following: a blood pressure device, a pulse oximeter, a heart rate monitor, a scale, a thermometer, a glucose meter, or the like. The health sensors 105 may be continuous use sensors (e.g., wearable devices) or single-use sensors. The health sensors 105 may have communication devices that permit them to communicate with other electronic devices over a network, e.g., a Bluetooth network, a Wi-Fi network, the Internet, or the like. The health sensors 105 may have position sensors.

The patient device 110 may be any electronic device capable of communicating with other electronic devices over a network. For example, the patient device 110 may be a laptop or desktop computer, an electronic tablet, a smartphone, a smartwatch, or the like. In some embodiments, the patient device 110 is the patient's personal device. In other embodiments, the patient device 110 is provided to the patient with the health sensors 105.

The patient device 110 can run a patient application 115. The patient application 115 may be an HTML document rendered by a web-browser, JavaScript code or Java code, or dedicated software, e.g., an installed application. The patient application 115 can cause the patient device 110 to automatically pair to, i.e., establish a wireless connection with, the health sensors 105 over a network. To facilitate pairing, the patient application 115 may have a sensor integration module. The sensor integration module may have, for each health sensor 105, a pairing procedure for automatically pairing the health sensor to the patient device 110 when the health sensor is powered on and within range of the patient device 110. The pairing procedure may include a unique identifier for the health sensor. The sensor integration module may be configurable in that pairing procedures for different health sensors 105 can be inserted or removed according to the testing routine of the patient. The sensor integration module can download pairing procedures for a wide variety of health sensors from a database of such pairing procedures.

When the patient opens the patient application 115 or initiates a testing procedure, the sensor integration module can activate a communication interface, e.g., a Bluetooth communication interface or a Wi-Fi communication interface, on the patient device 115. Using the communication interface, the sensor integration module can scan for devices in the vicinity that use the same communication interface. The sensor integration module can obtain a list of devices that are visible to the patient device 115. The list of devices may include an identifier, e.g., a MAC address or name, for each of the devices in the list. The sensor integration module can compare the identifiers in the list to known identifies for the health sensors 105 in the patient's testing routine. When the sensor integration module identifies matches, it can send connection requests to those health sensors. The connection requests can include authentication information, e.g., passwords, for the health sensors. The patient device 115 and the health sensors 105 can establish cryptographically secure connections by sharing secure link keys. The health sensors 105 and the patient device 115 can each store the secure link keys. Once the link keys are generated, authenticated Asynchronous Connectionless (ACL) links between the devices can protect exchanged data against eavesdropping. This can ensure that sensitive health measurement data is not stolen. The health sensors 105 and the patient device 115 can store the secure link keys indefinitely or for a predetermined period of time so that the health sensors and the patient device 115 can pair more quickly during subsequent testing sessions. After establishing the communication links, the patient application 115 can wirelessly communicate with the health sensors 105. For example, the patient application 115 can transmit control instructions to the health sensors 105 and obtain health measurement data from them.

The patient application 115 can also instruct the patient about how to properly take health measurements using the health sensors 105 and in which order to take such health measurements. The instructions may be audible, textual, pictorial, animated, or some combination thereof. The patient application 115 may have configurable settings that permit a patient to specify the format in which he or she prefers to receive the instructions. For example, a patient who is hard-of-hearing may choose to receive visual instructions rather than audible instructions.

In response to a user input in the patient application 115, the patient application 115 can initiate a testing routine. The testing routine may include a plurality of health measurements using a plurality of the health sensors 105. First, the patient application 115 may indicate which health sensor to use to take a first health measurement. The patient application 115 can display an image of the health sensor, announce the name of the health sensor, or describe what the health sensor looks like. The patient application 115 can determine that the patient selected the correct health sensor by detecting a change in the position of the health sensor.

The patient application 115 can then provide instructions to the patient regarding how the patient should position the health sensor in order to take a proper health measurement. For example, if the health sensor is a blood pressure device, the patient application 115 can provide instructions that indicate that the patient should position the blood pressure cuff on his or her upper right arm. If the health sensor is a pulse oximeter, the patient application 115 can provide instructions that indicate that the patient should position the pulse oximeter on his or her left index finger. The health sensor can transmit position data to the patient application 115, which can interpret the position data to determine whether the heath sensor should be adjusted relative to its current position, or whether it is positioned properly on the patient's body. If the health sensor is not positioned properly, the patient application 115 can provide additional, corrective instructions to the patient. For example, if the health sensor is a blood pressure device, the patient application 115 can provide instructions that indicate that the patient should adjust the position of the blood pressure cuff on his or her arm.

After the patient application 115 determines that the health sensor is properly positioned with respect to the patient's body, the health application can transmit control signals to the health sensor, if necessary. For example, if the health sensor is a blood pressure device, the patient application 115 can cause the patient device 110 to transmit a control signal to the cuff of the blood pressure device that causes the cuff to inflate. In some cases, the patient application 115 may not transmit control signals to the health sensor. For example, if the health sensor is a heart rate monitor, the heart rate monitor may begin collecting valid data as soon as it is correctly positioned on the patient's body, and it may not need an external control signal to operate. Likewise, passive devices such as scales and thermometers may begin collecting valid data as soon as they are correctly positioned.

While the health sensor obtains data from the patient, the patient application 115 can indicate the progress of the health measurement. The indication can be a visual indication, e.g., a progress bar or a textual percentage, or an audible indication of the same. The health sensor can transmit resultant health measurement data to the patient device 110. The patient application 115 can determine if the data is valid. Valid data may be data that falls within a predefined range. For example, a valid heart rate may be between 20 beats/minute and 220 beats/minute. If the data falls outside the predefined range, the patient application 115 can instruct the user to take the health measurement again. Valid data may also be data that has a particular characteristic. For example, if the health sensor is a scale, the patient application 115 may expect to receive a single data point indicating the patient's measured weight. If the data is instead time-series data with multiple data points, the patient application 115 may determine that the data is invalid, e.g., because the patient used the incorrect health sensor.

When the patient application 115 determines that it has received valid data for the health measurement, the patient application 115 can provide instructions for taking a second health measurement using a second health sensor. The process described above can be repeated for each of the health sensors in the patient's testing routine.

In some cases, the patient application 115 can provided instructions for taking a particular health measurement at a particular time of day, e.g., after the patient has eaten a meal. In such cases, the patient application 115 can notify the patient to take the health measurement at that time. The patient application 115 can also remind the patient to take measurements that are overdue.

In some cases, the patient may take the above-mentioned health measurements exclusively in the patient's home without supervision from a medical professional. If the patient does not have a mobile computing device or struggles navigating mobile operating systems, the health application 115 may be deployed on an electronic tablet that is shipped with the health sensors 105 in a customizable kit. The patient's HCP can determine the particular set of health sensors in the customizable kit based on the patient's medical needs. The health application 115 may be configured with a "workflow" that corresponds to the particular set of heath sensors in the kit. The workflow may be a set of procedures that cause the electronic tablet to automatically pair to the heath sensors 105 over a network, provide instructions about how to use each of the health sensors to take the health measurements in the patient's unique testing routine, obtain health measurement data generated by those health sensors, and parlay processed data results to the patient or to an HCP for education and/or therapeutic feedback. The workflow may be assembled in a modular fashion from pre-defined processing logic. If the patient's HCP prescribes additional health sensors to the patient, the patient can receive another shipment with the additional health sensors. The workflow on the patient's health application can be automatically reconfigured, e.g., over the cloud, to account for the patient's new combination of health sensors.

If the patient has his own patient device 110 and is comfortable using it, he can instead download the patient application 115 from the appropriate application store (e.g., the Apple App Store). Along with the shipment of health sensors 105 prescribed by the patient's HCP, the patient can receive a barcode or a quick response (QR) code that defines the unique combination of health sensors in the shipment and the order in which the patient should use those health sensors. The patient can scan the barcode or QR code using his patient device 110, and the health application 115 can configure its workflow based on the data encoded in the QR code. Alternatively, the patient's HCP can upload an electronic treatment plan accessible by the health application 115. The electronic treatment plan can, like the barcode or QR code, define the unique combination of health sensors prescribed to the patient by the patient's HCP. The electronic treatment plan can be associated with a health profile of the patient to which the HCP has access. The health application 115 can use the electronic treatment plan to generate a workflow corresponding to the unique combination of health sensors.

Analytics Layer

The patient application 115 can immediately transmit valid data that it receives from the health sensors to the computing system 120. The database 122 of the computing system 120 can store the data indefinitely or for a predetermined amount of time, e.g., 1 month, 2 months, 3 months, 4 months, 5 months, 6 months, 1 year, 2 years, 3 years, 4 years, 5 years, or more. The processor 124 and the machine learning module 126 can implement algorithms that use the patient data to generate predictions, analytics, alerts, and visualizations, as described in more detail in subsequent figures.

The algorithms may be customized for the patient. This may be especially useful for treating patients with multiple comorbidities (chronic disease states). For example, a patient with chronic obstructive pulmonary disorder (COPD), arterial fibrillation, and hypertension can have a profile of algorithms that determine the likelihood of arrhythmias and oxygenation/ischemic-related episodes. The service providers for such a patient may include emergency responders, health coaches, and cardiologists. A patient with diabetes and chronic heart failure, on the other hand, may have a set of algorithms that detect the onset of diabetic-related edema development and glucose instability. The service providers for such a patient may include endocrinologists, pharmacists, and therapeutics companies.

Figure 9A:
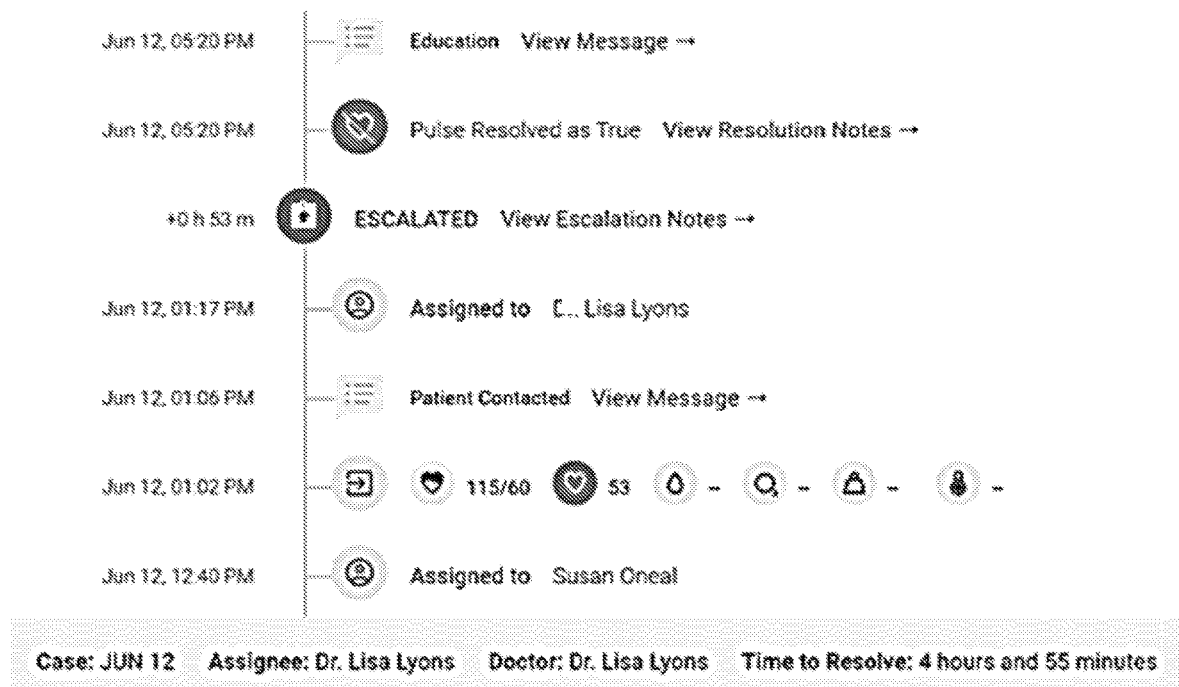
FIGS. 9A and 9B show patient alerts.

In some cases, the algorithms can generate alerts that are reviewed by analysts. FIG. 9A shows an example of a heart rate alert. In this example, the heart rate alert was generated when the computing system 120 determined that a patient's heart rate measurement was outside of an acceptable or normal range. The computing system 120 displayed the alert and the corresponding heart rate measurement on a triage platform monitored by analysts. The triage platform may be integrated into the HCP application 135, or it may be a separate application. The computing system 120 assigned the alert to analyst Susan. Susan reviewed the alert and the corresponding data and contacted the patient by sending a message to the patient through the patient application 115. Based on the patient interaction, Susan escalated the alert to physician Dr. Lisa, who determined that the alert was true (i.e., that the patient actually recorded the heart rate measurement that led to the alert). Finally, Dr. Lisa sent a message to the patient through the patient application 115. The message was an educational intervention containing strategies about how to avoid a low hear rate.

Figure 9B:
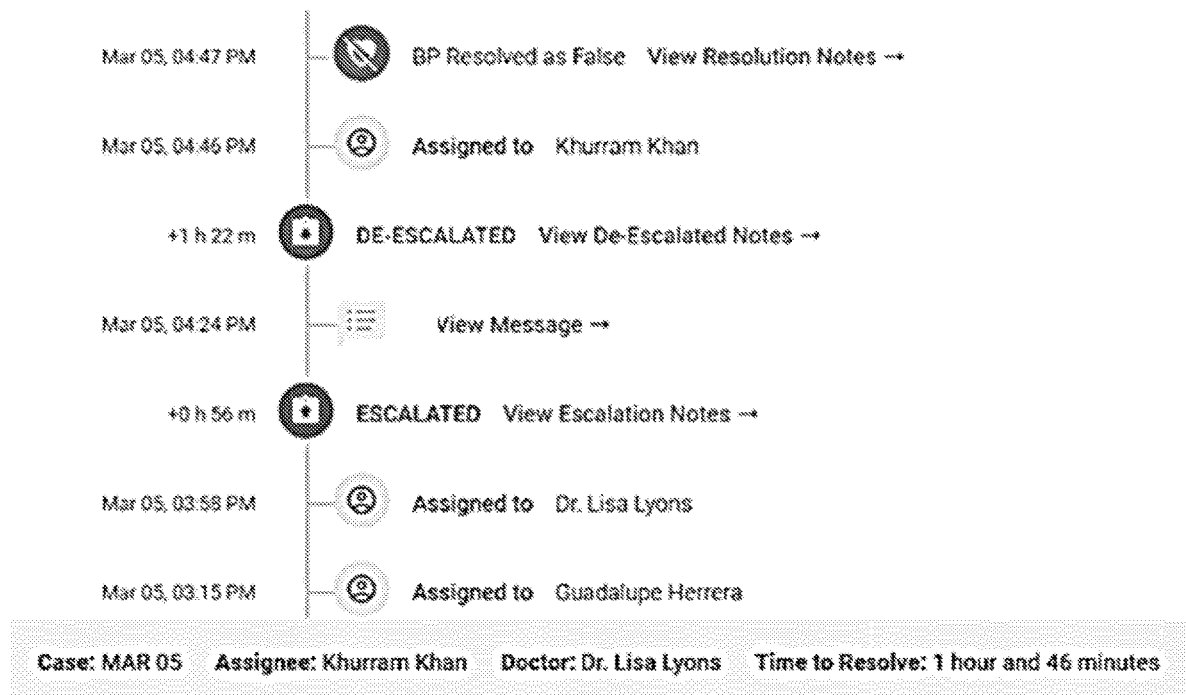

FIG. 9B shows an example of a systolic blood pressure alert that was eventually resolved as false.

HCP-Facing Layer

The computing system 120 can transmit data comprising the predictions, analytics, alerts, and visualizations to the HCP device 130, which runs the HCP application 135. The HCP application 135 can display the predictions, analytics, alerts, and visualizations on an electronic display of the HCP device, for consumption by an HCP.

Computing Devices

The computing devices described in reference to FIG. 1 may be servers, desktop or laptop computers, electronic tablets, mobile devices, or the like. The computing devices may be located in one or more locations. The computing devices may have general-purpose processors, graphics processing units (GPU), application-specific integrated circuits (ASIC), field-programmable gate-arrays (FPGA), or the like. The computing devices may additionally have memory, e.g., dynamic or static random-access memory, read-only memory, flash memory, hard drives, or the like. The memory may be configured to store instructions that, upon execution, cause the computing devices to implement the functionality of the computing devices. The computing devices may additionally have network communication devices. The network communication devices may enable the computing devices to communicate with each other and with any number of user devices, over a network. The network may be a wired or wireless network. For example, the network can be a fiber optic network, Ethernet® network, a satellite network, a cellular network, a Wi-Fi® network, a Bluetooth® network, or the like. In other embodiments, the computing devices can be several distributed computing devices that are accessible through the Internet. Such computing devices may be considered cloud computing devices.

Predicting Adverse Health Events

Figure 2:
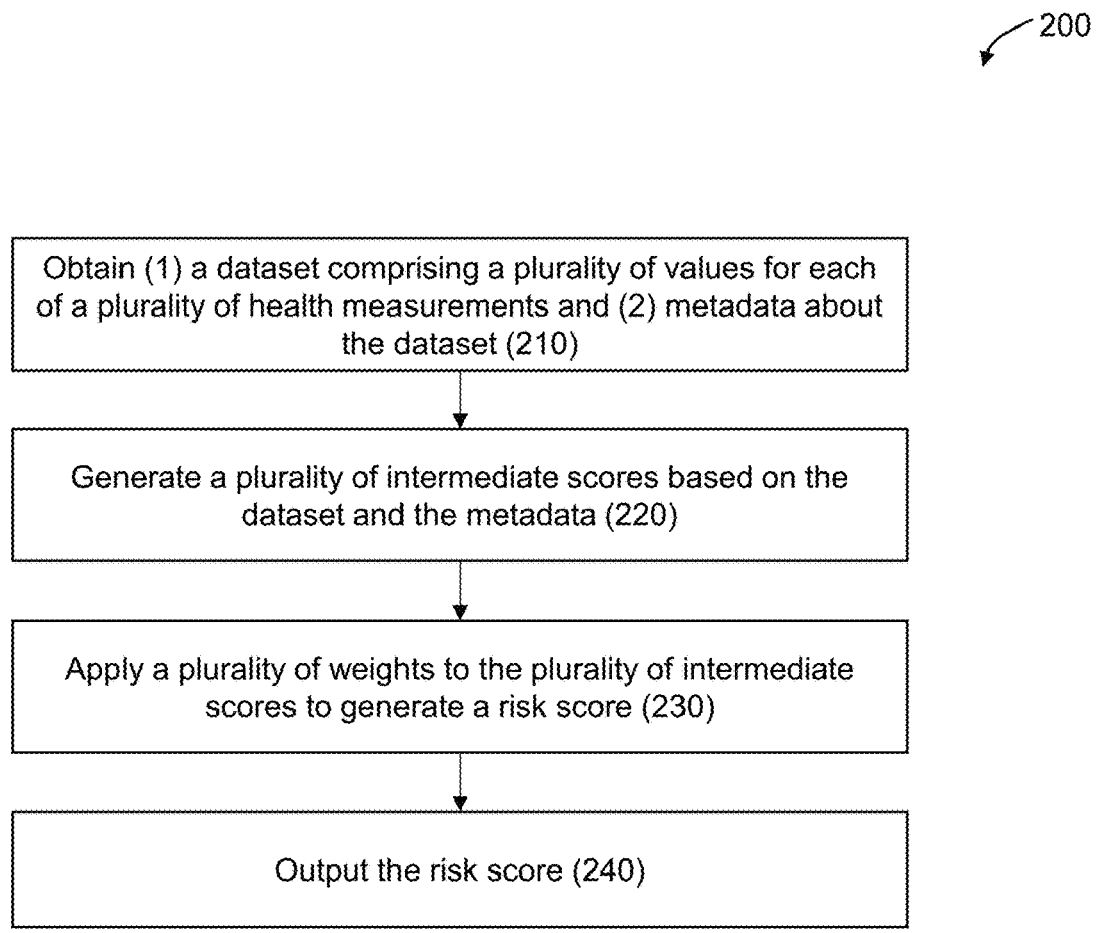
FIG. 2 is a flow chart of a process for predicting an adverse health event of a patient, according to some embodiments.

FIG. 2 is a flow chart of a process 200 for predicting an adverse health event of a patient, according to some embodiments. The process 200 can be performed by one or more appropriately programmed computers in one or more locations (e.g., the computing system 120 of FIG. 1). The adverse health event may be an event that leads to the hospitalization of the patient. For example, the adverse health event may be a stroke, blood clot, heart attack, seizure, pulmonary event, hyperglycemia/hypoglycemia event, edema, or the like. The adverse health event may be associated with a chronic condition of the patient (e.g., a pulmonary event when the patient has chronic obstructive pulmonary disorder (COPD)).

In an operation of process 200, the system can obtain a dataset including a plurality of values for each of a plurality of health measurements and metadata about the dataset (210). The system can obtain the dataset from a patient device (e.g., the patient device 110 of FIG. 1), which can temporarily store the dataset after the patient has taken health measurements using a plurality of health sensors (e.g., the sensors 105 of FIG. 1) that are wirelessly coupled to the patient device. Additionally or alternatively, the system can obtain the dataset from a wearable device of the patient. Additionally or alternatively, the system can obtain the dataset from an electronic medical record (EMR) of the patient.

The system can periodically obtain values for the plurality of health measurements. For example, the system can obtain new values every hour, day, week, or month. Additionally or alternatively, the system may be configured to automatically obtain new values immediately after such new values are available. That is, the system can obtain the values in real-time or substantially real-time after the health measurements are taken by the patient. The use of real-time or substantially real-time health data may result in more accurate and timely predictions of adverse health events than the use of stale data (e.g., data from a previous hospital visit). More accurate and timely predications may result in better health outcomes for patients due to early intervention.

The health measurements may include diastolic blood pressure, systolic blood pressure, oxygen saturation, heart rate, weight, blood glucose level, and the like. The health measurements may additionally include a quantity of alerts, escalations, or interventions. An escalation may result from the system detecting an out of range value for one of the health measurements. The escalation may involve an HCP reviewing the out of range value and any other relevant medical data of the patient. Escalations may or may not result in interventions. An intervention may involve an HCP contacting the patient or visiting the patient's home, the patient scheduling a medical appointment, or emergency services being called. The metadata of the dataset may include a measure of adherence to a testing routine including the plurality of health measurements. The measure of adherence may indicate, for example, a quantity of testing routines or individual health measurements that the patient missed over a particular time period.

In some cases, the system can also obtain a medical history of the patient. The system can obtain the medical history from the patient's EMR and supplement it with answers from patient questionnaires. The system can create a patient profile from the medical history and questionnaire answers. FIGS. 10A, 10B, and 10C show an example of a patient profile. The patient profile may contain data about the patient's chronic conditions, lab values, medical system utilization, oncology results, falls, and social factors (FIG. 10A). The patient profile may also contain answers to subjective health questions (FIG. 10A), vaccination records (FIG. 10B), and medications (FIG. 10C). The patient profile may also contain a high-level, qualitative assessment of the patient's health. The qualitative assessment may indicate that the patient is maintaining his or her health state, or that the patient's health is improving or declining. The qualitative assessment may be based on trends in the patient's risk score, which is described in more detail below. For example, a patient with declining risk scores may have improving health.

Figure 3:
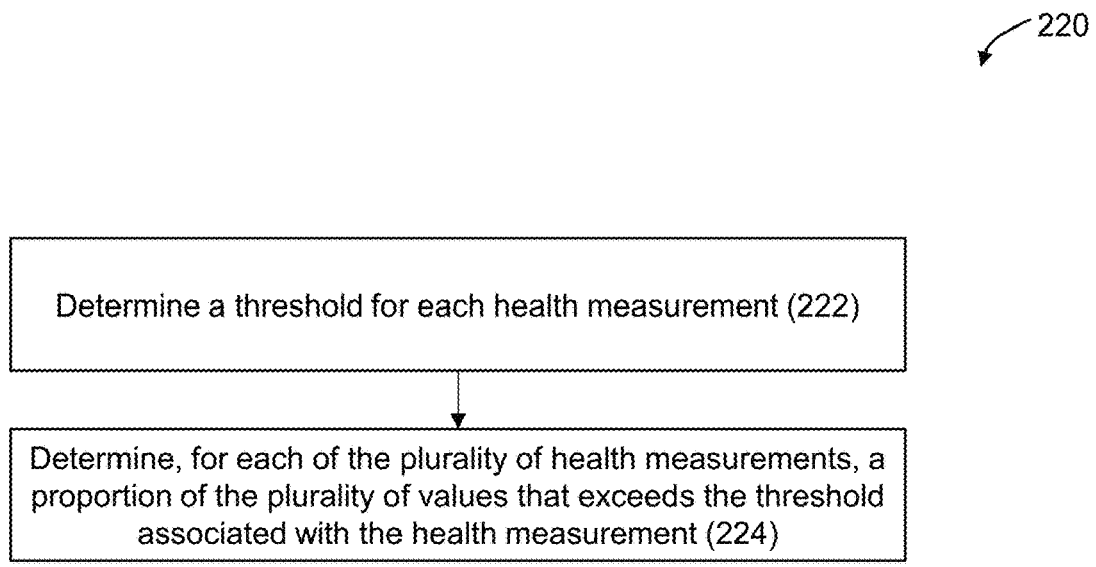
FIG. 3 is a flow chart of a process for generating intermediate scores that contribute to a patient risk score, according to some embodiments.

The system can use data from the patient profile in subsequent operations of the process 200. For example, the system can use data points from the patient profile as separate inputs alongside the values from the dataset, or it can use such data points to determine ranges or weights for the patient as described in greater detail below. The system can generate a plurality of intermediate scores based on the dataset and the metadata (220). FIG. 3 is a flow chart of a process 220 for generating the plurality of intermediate scores, according to some embodiments. The process 220 can be performed by one or more appropriately programmed computers in one or more locations (e.g., the computing system 120 of FIG. 1).

In an operation of process 220, the system can determine a range for each of the plurality of health measurements (222). The range may include values that are considered normal or healthy for an average person, for a demographic group (e.g., age, race, sex, etc.) comprising the patient, for people with the patient's condition or disease (e.g., heart disease, COPD, etc.), or for the patient himself, as determined by the patient's healthcare provider. That is, the range may be patient-specific or based in part on the patient's medical history (e.g., data from the patient's health profile shown in FIG. 10). For example, the range may be based on a baseline for the patient as determined by the patient's HCP. In some cases, the range may be dynamic. That is, the system can adjust the range over time. For example, the system can adjust the range as the patient's general health improves or declines or as the patient ages. The range may be a function of one or more inputs. For example, the range for blood pressure for the patient may be a function of the patient's age, weight, diet, and medication. The function may be a statistical function or a machine learning algorithm.

In another operation of process 220, the system can determine, for each health measurement, the proportion of the values for the health measurement that exceed the threshold for the health measurement (224). The system can determine the proportion by dividing the quantity of values that exceed that threshold within a time period by the total quantity of values recorded by the patient in that time period. The time period may be about 1 week, 2 weeks, 3 weeks, 4 weeks, 1 month, 2 months, 3 months, 4 months, 5 months, 6 months, 1 year, or more. The time period may be the preceding 1-month period. The time period may be the quantity of preceding days in the current month (e.g., 20 days if the current date is March 20).

In other embodiments, the system can generate the plurality of intermediate scores in a different way. For example, the presence of documented medication adherence, clinical interventions, and educational interventions within a set time window may contribute to a rehabilitation intermediate score. The rehabilitation intermediate score may counteract the presence of vital deterioration, unaddressed clinical alerts, and medication nonadherence, which are subsets of a deterioration intermediate score. Both of the aforementioned intermediate scores can be used in place of, or in conjunction with, a holistic risk score to assess a patient's overall health level. In still other embodiments, the system may not generate intermediate scores and may instead use the raw health measurement values in subsequent operations of the process 200.

Returning to FIG. 2, the system can apply a plurality of weights to the plurality of intermediate scores to generate a risk score (230). The risk score may indicate the likelihood that the patient will experience the adverse health event within a specified time period. The time period may be the next day, the next week, the next month, the next two months, the next three months, the next four months, the next year, or more. As mentioned above, in one example, the intermediate scores are based on health measurement values from the preceding days in the current month. Therefore, the risk score in one month may be independent from the risk score in another month. The system can update the risk score for a particular month as it obtains new data during that month (e.g., as it obtains daily health measurement values from the patient).

In some embodiments, the weights are discrete weights. Each discrete weight may be associated with a particular health measurement. The weights may be equal, or the weights may be different. The weights may be patient specific. That is, the weights may be based on the patient's unique health circumstances and/or medical history (e.g., data from the patient's health profile shown in FIG. 10). The system may apply large weights to health measurements that have a large positive correlation with the health risk of the patient. For example, the system may apply a large weight to the blood glucose level of the patient if the patient has diabetes or to the diastolic and systolic blood pressure of the patient if the patient has hypertension. The system can add the weighted intermediate scores together to generate the risk score. The resulting risk score may be a real number. Large real numbers may be indicative of a high risk of an adverse health event and low real numbers may be indicative of a low risk of an adverse health event. The distribution of real-numbered risk scores for a plurality of patients may be used as a guideline to define risk levels. For example, the system can determine that a patient with a risk score below the $25^{th}$ percentile is at low risk of an adverse health event, while a patient with a risk score above the $75^{th}$ percentile is at high risk of an adverse health event. The risk score may be qualitative risk score, e.g., "low risk," "moderate risk," "moderate high risk," "high risk," or "very high risk" of an adverse health event.

In other embodiments, the system provides the plurality of intermediate scores to a machine learning algorithm that generates the risk score. The machine learning algorithm may represent a complex function that defines how the intermediate scores are combined and weighted. The machine learning algorithm may be a supervised machine learning algorithm. The supervised machine learning algorithm may be trained on prior data from the patient, on prior data from similar patients, or a combination thereof. The prior data may include health measurement values for first time periods and instances of adverse health events during second subsequent time periods. The system can train the supervised machine learning algorithm by providing examples of health measurement values from the first time periods to an untrained or partially trained version of the algorithm to generate predicted outputs that indicate whether the patient will experience adverse health events during the second time periods. The system can compare the predicted outputs to the known outputs (i.e., whether the patient actually experienced adverse health events during the second time periods), and if there is a difference, the system can update the parameters of the supervised machine learning algorithm. The supervised machine learning algorithm may be a regression algorithm, a support vector machine, a decision tree, a neural network, or the like. In cases in which the machine learning algorithm is a regression algorithm, the weights may be regression parameters. The supervised machine learning algorithm may be a binary classifier that predicts whether or not the patient will experience an adverse health event. The binary classifier may generate a probabilistic risk score between 0 and 1. In some cases, the system may map the probabilistic risk score to a qualitative risk category. Alternatively, the supervised machine learning algorithm may be a multi-class classifier that predicts a qualitative risk category directly.

The machine learning algorithm may be an unsupervised machine learning algorithm. The unsupervised machine learning algorithm may be capable of identifying patterns in the intermediate scores. For example, it may be capable of identifying a set of intermediate scores that is an outlier as compared to other sets of intermediate scores from the patient or from other similar patients. If the unsupervised machine learning algorithm determines that a particular set of intermediate scores from the patient is an outlier, the system may determine that the patient is at high risk of an adverse health event. On the other hand, a set of intermediate scores that is consistent with previous intermediate scores for the patient may indicate that the patient is not at low risk of an adverse health event. The unsupervised machine learning algorithm may be a clustering algorithm, an isolation forest, an autoencoder, or the like.

In generating the final risk score, the system may also consider certain social factors, including the patient's location, living arrangement, food security, access to care, and primary language. The system can quantify these factors and add them to the intermediate scores or provide them as additional input to the machine learning algorithms described above. The system may also consider any data in the patient's profile (FIG. 10).

The system can output the risk score or a graphical representation thereof on the graphical user interface of a computing device (240). The computing device may be the computing device of an HCP. The HCP may be the patient's primary care physician or another physician managing the patient's care. The HCP can use the risk score to alter treatment, proactively intervene, or triage the patient.

Figure 4:
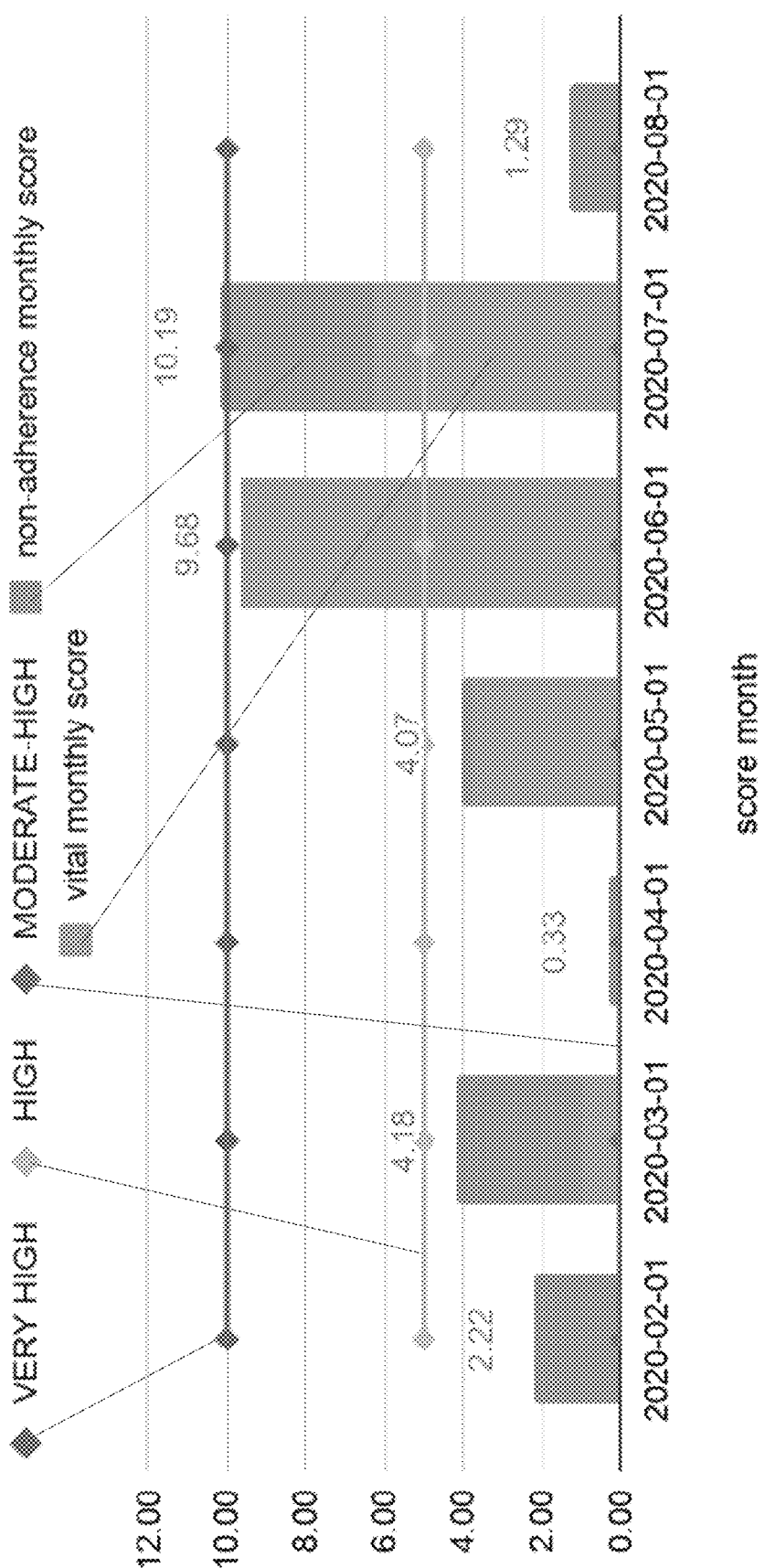
FIG. 4 is a bar graph that shows risk scores for a patient.

An example of a graphical representation of the risk score is depicted in FIG. 4. FIG. 4 is bar graph that shows the monthly risk scores for a patient from February 2020 to August 2020. The bar graph shows that the patient's risk score generally increased over time from 2.22 in February 2020 to 10.19 in July 2020, followed by a significant drop to 1.29 in August 2020. The bars in the bar graph show the contribution of vital signs and non-adherence to the total risk score. In June 2020, the patient's high risk score was solely the result of vital sign alerts, while the patient's high risk score in July 2020 was attribute to both vital sign alerts and non-adherence to the patient's testing routine. The bar graph shows that risk scores of 10 and above are very high and that risk scores between 5 and 10 are moderately high.

In addition to the predictive risk score generated during the process 200, the system described herein can compute a baseline risk score for a patient. The baseline risk score may be descriptive rather than predictive. The baseline risk score may be less variable than the predictive risk score. The baseline risk score can be used to group patients into risk tiers. FIG. 5A and FIG. 5B show factors that contribute to the baseline risk score, according to some embodiments. The factors may include chronic conditions (e.g., dementia, hypertension, liver disease, etc.), medical system utilization (e.g., emergency room visits), cancer, falls, social determinants (e.g., location and food insecurity), answers to subjective health questions, lab values, age, and the like. Each factor may contribute one or more points to the baseline risk score if the factor is applicable to the patient.

EXAMPLE

FIG. 6 shows the calculation of a risk score, according to some embodiments. The risk score is based on the following factors: the patient's diastolic and systolic blood pressure, oxygen saturation, heart rate, weight, glucose, escalations per submission, interventions per submission, and adherence to the testing routine comprising these health measurements. For each health measurement type, the system determines the proportion of measurements during a one-month period that are out-of-range for the patient. The system also determines the quantity of escalations per submission and the quantity of interventions per submission. A submission is the successful completion of the patient's testing routine on a particular day. The system also determines the patient's non-adherence to the testing routine, which is the proportion of days in the one-month period in which the patient did not complete the testing routine. The system then applies weights to each of the factors, adds the weighted factors together, and multiplies the result by 10. In this example, the system applies equal weights to all of the factors.

In this example, patient Jane Doe had out-of-range measurements for diastolic blood pressure (10% of measurements out-of-range) and weight (50% of measurements out-of-range). 30% of Jane Doe's submissions resulted in escalations, and 20% of her submissions resulted in interventions. Finally, Jane Doe failed to follow her testing routine on 10% of days in the one-month period. The system applied equal weights to these factors, added the weighted factors together for a subtotal of 1.2, and multiplied the subtotal of 1.2 by 10 for a resulting monthly risk score of 12.

Figure 7:
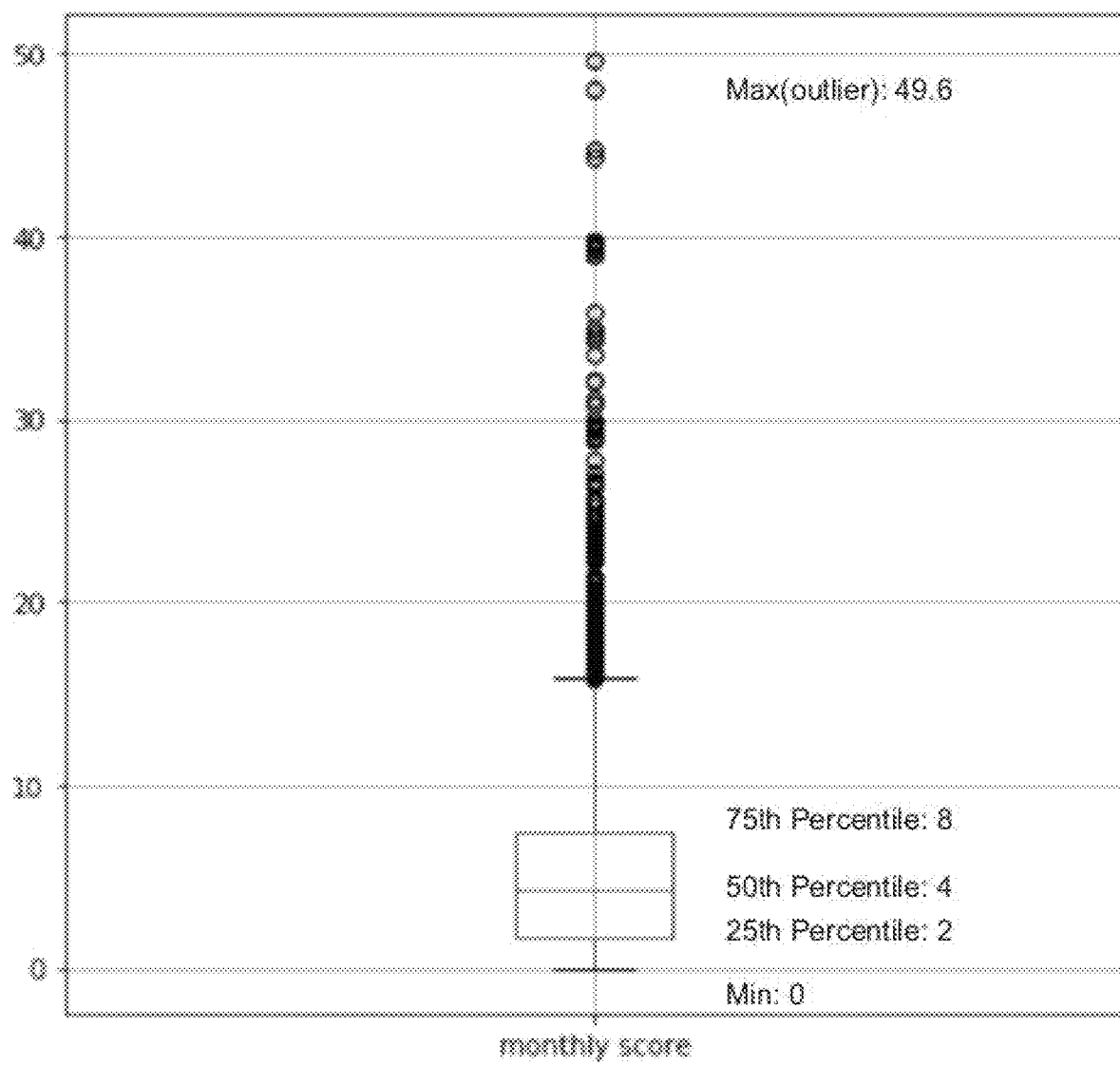
FIG. 7 shows a distribution of monthly risk scores for various patients.

FIG. 7 shows a distribution of approximately 28,000 monthly risk scores for various patients. The maximum monthly risk score was 49.6. The $75^{th}$ percentile monthly risk score was 8. The $50^{th}$ percentile monthly risk score was 4. The $25^{th}$ percentile monthly risk score was 2. And the minimum monthly risk score was 0. This distribution was used as a guideline to define qualitative risk levels. "Moderate High" risk was defined as score of 0-4. "High" risk was defined as scores of 5-9. And "Very High" risk was defined as score of 10 or greater.

Neural Networks

The present disclosure describes the use of machine learning algorithms to generate a risk score that indicates the likelihood that a patient will experience an adverse health event. The machine learning algorithms may be neural networks. Neural networks may employ multiple layers of operations to predict one or more outputs (e.g., a risk score) from one or more inputs (e.g., health measurement and socioeconomic data). Neural networks may include one or more hidden layers situated between an input layer and an output layer. The output of each layer can be used as input to another layer, e.g., the next hidden layer or the output layer. Each layer of a neural network may specify one or more transformation operations to be performed on input to the layer. Such transformation operations may be referred to as neurons. The output of a particular neuron may be a weighted sum of the inputs to the neuron, adjusted with a bias and multiplied by an activation function, e.g., a rectified linear unit (ReLU) or a sigmoid function. The output layer of a neural network may be a softmax layer that is configured to generate a probability distribution over two or more output classes.

Training a neural network may involve providing inputs to the untrained neural network to generate predicted outputs, comparing the predicted outputs to expected outputs, and updating the algorithm's weights and biases to account for the difference between the predicted outputs and the expected outputs. Specifically, a cost function may be used to calculate a difference between the predicted outputs and the expected outputs. By computing the derivative of the cost function with respect to the weights and biases of the network, the weights and biases may be iteratively adjusted over multiple cycles to minimize the cost function. Training may be complete when the predicted outputs satisfy a convergence condition, e.g., a small magnitude of calculated cost as determined by the cost function.

Computer Systems

Figure 8:
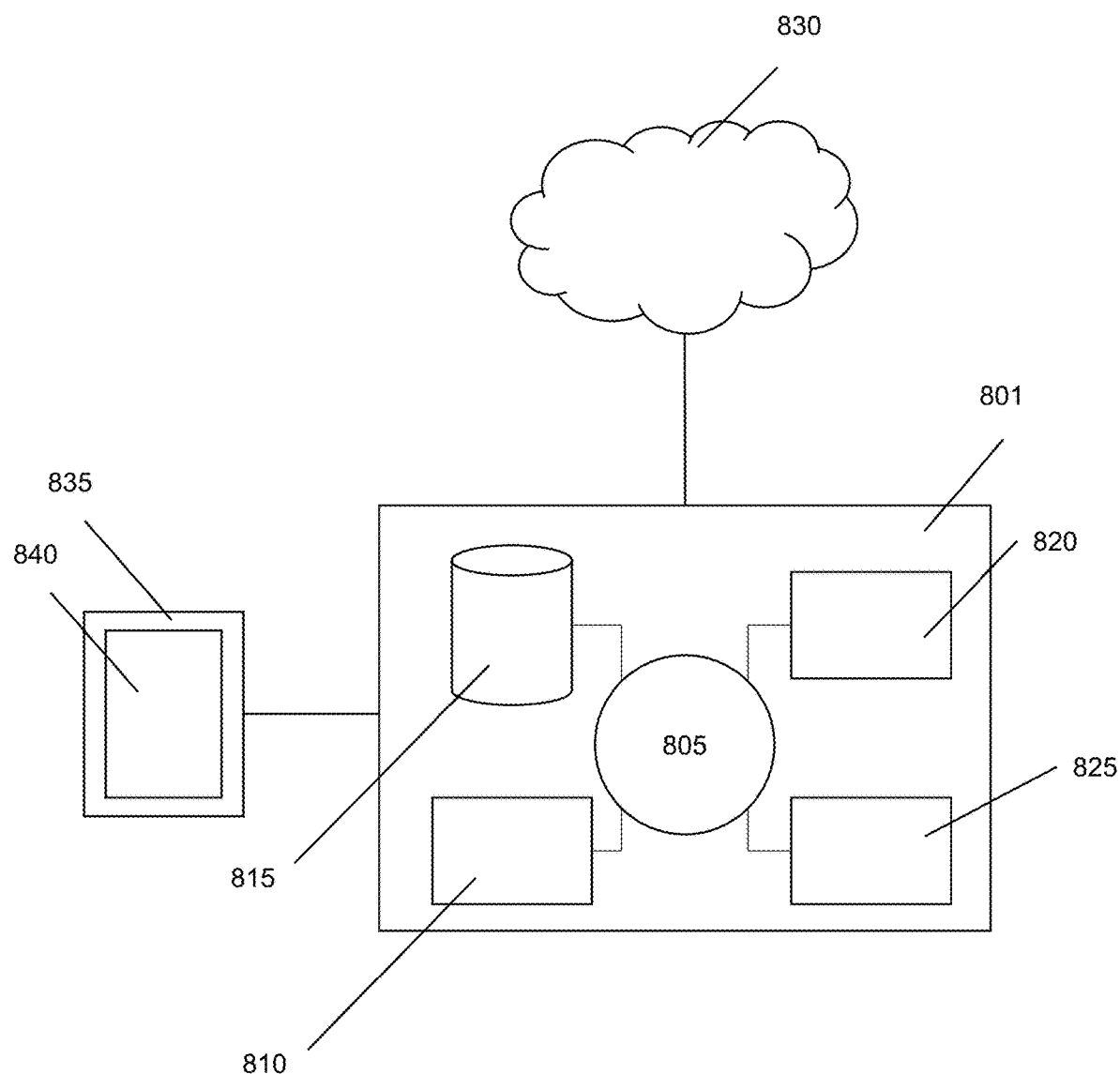
FIG. 8 shows a computer system that is programmed or otherwise configured to implement methods provided herein.

The present disclosure provides computer systems that are programmed to implement methods of the disclosure. FIG. 8 shows a computer system 801 that is programmed or otherwise configured to predict an adverse health event of a patient. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., the patient device 110 of FIG. 1). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine-readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processer adapted to execute the code or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, health measurement instructions to a patient or a risk score and corresponding visualizations to an HCP. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805. The algorithm can, for example, an algorithm that implements the process 200 of FIG. 2.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for predicting an adverse health event of a subject, comprising:
    (a) obtaining a dataset from one or more sources, wherein the dataset comprises a plurality of values for health measurements of the subject;
    (b) generating metadata about the dataset, wherein the metadata comprises a measure of adherence to a testing routine comprising the health measurements;
    (c) generating a plurality of intermediate scores based on the dataset and the metadata;
    (d) using a trained machine learning algorithm to generate a risk score by applying a plurality of weights to the plurality of intermediate scores, wherein the risk score is indicative of whether the subject will experience the adverse health event; and
    (e) outputting the risk score on a graphical user interface of a computing device, wherein (b)-(e) are performed within 30 days of (a), and
    (f) determining whether to initiate a medical intervention for the subject based at least in part on the risk score.

2. The method of claim 1, wherein the dataset and the metadata are obtained from a remote computing device of the subject.

3. The method of claim 1, wherein each weight of the plurality of weights is associated with one of the health measurements.

4. The method of claim 3, wherein the plurality of weights is specific to the subject.

5. The method of claim 4, wherein the plurality of weights is based at least in part on a medical history of the subject.

6. The method of claim 1, wherein the machine learning algorithm comprises a classifier.

7. The method of claim 1, wherein the machine learning algorithm is a regression algorithm.

8. The method of claim 1, wherein the measure of adherence is based at least in part on a quantity of missing values in the plurality of values.

9. The method of claim 1, wherein the range is a patient-specific range.

10. The method of claim 1, wherein the range is based at least in part on a medical history of the subject.

11. The method of claim 1, wherein the range is based at least in part on a baseline value for the subject.

12. The method of claim 1, wherein the health measurements comprises diastolic blood pressure, systolic blood pressure, oxygen saturation, heart rate, weight, or glucose.

13. The method of claim 1, further comprising determining a qualitative risk level associated with the risk score based on a distribution of risk scores of a plurality of subjects including the subject.

14. The method of claim 1, wherein each of the plurality of weights is the same.

15. The method of claim 1, wherein at least two of the plurality of weights are different.

16. The method of claim 1, wherein the one or more sources comprises (i) electronic medical records (EMR), (ii) a questionnaire response database, (iii) an electronic device which is configured for the subject uses to use to input data, (iv) a wearable device which is configured to be worn by the subject, or (v) one or more sensors that are configured to collect health measurements of the subject.

17. The method of claim 1, wherein the machine learning algorithm is an unsupervised machine learning algorithm, wherein the unsupervised machine learning algorithm is configured to compare the plurality of intermediate scores to a plurality of previous intermediate scores.

18. The method of claim 1, wherein the intermediate scores are based at least in part on a range for each of the health measurements, wherein the range dynamically adjusts responsive to changes in the subject's health.

19. One or more non-transitory computer storage media storing instructions that are operable, when executed by one or more computers, to cause the one or more computers to perform operations for predicting an adverse health event of a subject, comprising:
 (a) obtaining a dataset from one or more sources, wherein the dataset comprises a plurality of values for health measurements of the subject;
 (b) generating metadata about the dataset, wherein the metadata comprises a measure of adherence to a testing routine comprising the health measurements;
 (c) generating a plurality of intermediate scores based on the dataset and the metadata;
 (d) using a trained machine learning algorithm to generate a risk score by applying a plurality of weights to the plurality of intermediate scores, wherein the risk score is indicative of whether the subject will experience the adverse health event; and
 (e) outputting the risk score on a graphical user interface of a computing device, wherein (b)-(e) are performed within 30 days of (a), and
 (f) determining whether to initiate a medical intervention for the subject based at least in part on the risk score.

20. A system comprising one or more computers and one or more storage devices storing instructions that are operable, when executed by the one or more computers, to cause the one or more computers to perform operations for predicting an adverse health event of a subject, comprising:
 (a) obtaining a dataset from one or more sources, wherein the dataset comprises a plurality of values for health measurements of the subject;
 (b) generating metadata about the dataset, wherein the metadata comprises a measure of adherence to a testing routine comprising the health measurements;
 (c) generating a plurality of intermediate scores based on the dataset and the metadata;
 (d) using a trained machine learning algorithm to generate a risk score by applying a plurality of weights to the plurality of intermediate scores, wherein the risk score is indicative of whether the subject will experience the adverse health event; and
 (e) outputting the risk score on a graphical user interface of a computing device, wherein (b)-(e) are performed within 30 days of (a), and
 (f) determining whether to initiate a medical intervention for the subject based at least in part on the risk score.

* * * * *